United States Patent [19]

Hersom et al.

[11]  4,234,537

[45]  Nov. 18, 1980

[54] STERILIZATION OF PARTICULATE SOLID MATERIALS

[75] Inventors: Albert C. Hersom; John E. Brittain, both of Beaconsfield; Raymond Darlington, Crawley, all of England

[73] Assignee: Societe d'Assistance Technique pour Produits Nestle S.A., Lausanne, Switzerland

[21] Appl. No.: 906,775

[22] Filed: May 17, 1978

[30] Foreign Application Priority Data

Dec. 23, 1977 [GB] United Kingdom ............... 53759/77

[51] Int. Cl.³ .......................... A23L 3/16; A61L 2/06; A61L 2/26
[52] U.S. Cl. .................................... 422/26; 426/511; 426/519; 426/521
[58] Field of Search ...................... 422/26, 27, 31, 32; 426/521, 519, 511, 335, 331, 320

[56] References Cited

U.S. PATENT DOCUMENTS

| | | | |
|---|---|---|---|
| 3,088,179 | 5/1963 | Leuthner | 426/521 |
| 3,159,495 | 12/1964 | Japikse | 426/521 |
| 3,992,148 | 11/1976 | Shore et al. | 426/521 |
| 3,994,685 | 4/1976 | Lödige et al. | 422/26 |
| 4,055,673 | 10/1977 | Mueller et al. | 426/519 |
| 4,059,919 | 11/1977 | Green | 426/519 |

*Primary Examiner*—Bradley R. Garris
*Attorney, Agent, or Firm*—Christel, Bean & Linihan

[57] ABSTRACT

A batch process for the sterilization of particulate solid materials, in which a batch of particulate solid material to be sterilized is introduced into a rotary vessel shaped so that rotation of the vessel imparts a tumbling action to the solid material; the solid material is heated in the vessel while rotating the same to subject the material to a tumbling action; a lubricant liquid is injected under pressure into the vessel at a temperature in excess of the temperature of the solids; the lubricant liquid and solid material are held at a sterilization temperature while maintaining the tumbling action; and the sterilized solid material is withdrawn from the vessel under aseptic conditions.

11 Claims, 1 Drawing Figure

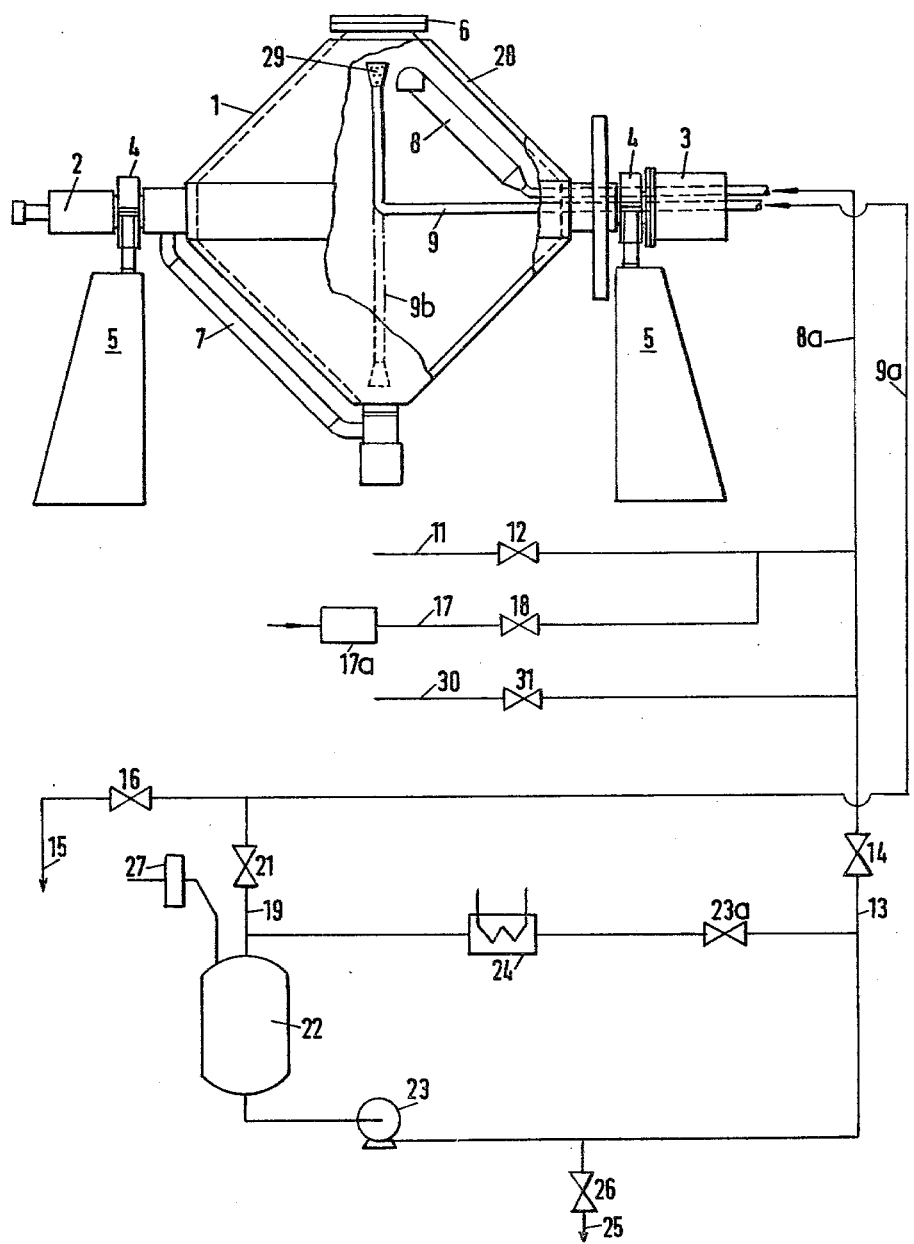

STERILIZATION OF PARTICULATE SOLID MATERIALS

This invention relates to the sterilization of particulate solid materials.

The invention relates particularly to the preparation of sterile cooled solid materials for human or animal food, which are aseptically packed in cans or other containers after sterilization, sterility being maintained until packaging is complete thereby avoiding the need for in-can sterilization as a subsequent operation. However, the invention is also applicable to other uses where sterility is to be achieved during a heat treatment process, such as in the preparation of chemical and particularly pharmaceutical products.

In United Kingdom Patent Specification No. 1 445 942 there is described and claimed a batch process for the sterilization of particulate solid materials, in which a batch of particulate solid material to be sterilized is introduced into a rotary vessel shaped so that rotation of the vessel imparts a tumbling action to the solid materials, the solid material is heated in the vessel while rotating the same to subject the material to a tumbling action, the heating being at least partly by the introduction of steam into the vessel to condense therein, the condensate and solid material is held at a sterilization temperature while maintaining the tumbling action and the sterilized solid material is withdrawn from the vessel under aseptic conditions.

It has been discovered that there is a need for a liquid to be present in such a process to minimise damage to the solid particulate material as this softens in the later stages of heating and that the condensate is not normally sufficient for this purpose. It has also been found that the presence of an appreciable quantity of water, added during initial loading of the vessel, slows down heating by inhibiting access of the steam to the solid particles.

According to the present invention there is provided a process for the sterilization of particulate solid materials, in which a batch of particulate solid material to be sterilized is introduced into a rotary vessel shaped so that rotation of the vessel imparts a tumbling action to the solid material; the solid material is heated in the vessel while rotating the same in order to subject the material to a tumbling action; a lubricant liquid is injected under pressure into the vessel at a temperature in excess of the temperature of the solids; the lubricant liquid and solid material are held at a sterilization temperature while maintaining the tumbling action, and the sterilized solid material is withdrawn from the vessel.

Preferably, the heating is partly by direct introduction of steam into the vessel to condense therein.

The solid materials are preferably withdrawn from the vessel under aseptic conditions and may be cooled before withdrawal. This cooling may take place under positive pressure and the vapour in the vessel may be replaced during the cooling by a sterile gas fed in through a sterilizing filter.

Certain solid materials may be heated in the initial stages without a lubricant, but in some cases a small amount of lubricant may need to be added to the initial batch of particulate solid material.

The lubricant itself may be water or cooking liquid kept from a previous batch and reheated, and in certain cases the lubricant, or some of it, may be an oil.

The lubricant to be injected is normally heated to its operating temperature during a period of time when steam is not being used in the main process and by this means peak demands on the steam plant are kept to a minimum.

It is preferred that the lubricant be heated in a sterile heating circuit, from which it is injected into the vessel and into which liquid withdrawn from the vessel is re-introduced. If this circuit and its contents are maintained sterile, there is no need for re-sterilization of the liquid lubricant to be injected after a shut-down.

It will be seen that according to the invention, the particulate solid material is heated rapidly, usually by the injection of steam, and this speed of heating minimises damage to the solids. As soon as the solids have been softened by the heating process, additional lubricant liquid is added, and this liquid is injected hot so that it supplements the heat contributed from the steam and additionally prevents excessive damage to the particles through attrition caused by the tumbling action.

The vessel may be rotated continuously during the heating and holding stages to maintain the tumbling action, or, alternatively, it may be intermittently rotated on a periodic basis.

The invention will be further described with reference to the accompanying drawing, which is a circuit diagram showing the principal features of a preferred form of apparatus for putting the invention into effect.

A tumbling vessel is shown at 1, and it may be assumed that this vessel is substantially the same as that described in our United Kingdom Pat. No. 1 445 942, previously referred to. This vessel has hollow trunnions as indicated at 2 and 3, mounted on bearing blocks 4 on support platforms 5. The vessel has a feed and access aperture 6 and a solids discharge duct 7 which feeds out through the hollow trunnion 2. The trunnion 3 carries lines leading to an inlet nozzle 8 and a withdrawal and venting pipe 9 carrying a bell mouth or other filter 29. The nozzle 8 may be used for injection of steam along a line 8a from a line 11 via a valve 12, or alternatively for the introduction of hot lubricant liquid from a line 13 via a valve 14. It may also be used for the provision of sterile air via a sterilizing filter 17a, line 17 and valve 18 or for sterile sauce or liquids through pipe 30 and valve 31. The pipe 9 leads to a line 9a for withdrawal of gases or liquids to a vent or drain line 15 via a valve 16. Line 9a also serves for the withdrawal of lubricant from vessel 1 to vessel 22 via valve 21 and pipe 19. For this purpose of withdrawing liquid the pipe 9 is moved to the position shown dotted and indicated at 9b in the drawing with the filter 29 near the bottom of the vessel 1.

Other details of the description of the vessel 1 and its associated equipment can be found in the patent specification No. 1 445 942 originally referred to, and the contents of which are imported by reference. A pressure vessel 22 contains the lubricant which may be heated by circulation via pump 23, a valve 23a and heat exchanger 24, then returning to the pressure vessel via pipe 19. The heat exchanger may be either an indirect heat exchanger or a steam injector may provide direct heat exchange. This constitutes a heating loop which can remain sterile if required. A sterilizing vent filter is shown at 27 on the vessel 22. A drain or outlet line 25 is shown controlled by a valve 26' which is opened when it is desired to empty the vessel 22. The vessel 22 also includes an upper level limit probe which controls the valves 21 and 16 so that when liquid is being returned via line 9a the vessel 22 is only filled to a level and excess liquid is directed to drain via line 15.

In operation, a charge of particulate material is introduced via the aperture 6 into the vessel 1, and with this charge there may, if required, be introduced a minimum amount of lubricant liquid, which may be water, oil or liquid from the vessel 22. The lubricant may be introduced via aperture 6 or via the inlet nozzle 8. The charge is heated by injection of steam through the inlet nozzle 8 while tumbling the charge of material by rotating the vessel 1, and this rotation may be either continuous or intermittent. As the solid material approaches sterilizing temperature, it becomes more subject to damage from the tumbling action and it becomes necessary to introduce the sterilizing liquid from the vessel 22 and this is achieved by opening the valve 14 and closing valve 23a so that the hot sterilizing liquid is injected under pressure via the nozzle 8. Air and steam displaced from the vessel leave via the pipe 9. Air to replace the liquid lost from the vessel 22 passes in through the sterilizing filter 27 so that sterility within the liquid circuit is maintained. The liquid in the vessel 22 is maintained at a temperature somewhat above the sterilizing temperature of the solid charge, so that it continues to heat the solid charge by supplementing the steam. The heating process is terminated when the sterilizing temperature has been held for a sufficient time, as judged by an $F_o$ meter which integrates the sterilization temperature with time and automatically controls the apparatus to finish the sterilization step at a preset value, e.g. 20 minutes at 250° F. (or equivalent sterilization value). The solids, condensate and lubricant are then cooled by circulating cold water in the jacket 28 of vessel 1. The cooled sterile liquid component is recovered by pressure transfer through line 9 valve 21 and line 19 into the vessel 22 whilst the line 9 is in the lowest position 9b with the filter 29 in the liquid. Any excess liquor beyond that required to fill the vessel 22 is directed by transfer via valve 16 and line 15. When the liquid is accumulated in vessel 22 it may be reheated by circulation through the heating loop, i.e. through pump 23 and heat exchanger 24. This heating may be a comparatively slow process as there is likely to be some delay before there is a further demand for hot liquid.

It will be appreciated that a hot liquid circuit such as illustrated may be used to service more than one vessel 1, provided they are all operating the same process.

The charge in the vessel 1 is then further treated, e.g. by introduction of a cold sterile sauce via line 30 and valve 31, and the finally treated charge is removed via the line 7 and the trunnion 2. This discharge line formed by these will of course have been sterilized during the course of the treatment so that sterility is maintained.

EXAMPLE 1

The product "Carrots in cream sauce" is prepared by loading into the vessel 1 a mixture of 91% of weight of fresh or frozen diced or sliced carrots, and 9% of weight of water. The lid 6 on vessel 1 is closed and the vessel is rotated at three revolutions per minute whilst injecting steam through nozzle 8 to maintain a headspace temperature of 130° C. After approximately 30 seconds, water preheated to 130° C., is injected via pump 23, valve 14 and nozzle 8, into the headspace of the vessel. Rotation of vessel 1 continues until the $F_o$ reaches the desired value. When the steam entering through nozzle 8 is turned off, sterile air is introduced at a pressure equivalent to 30 lbs per square inch to vent steam from the headspace. Cooling water is introduced into the jacket of vessel 1 until the temperature of the contents of the vessel reach 60° C. At this point the rotation of vessel 1 is stopped and the filter head 29 is lowered, the air pressure reduced to 12 to 15 psig and valve 16 is opened so that the surplus lubricant and condensate is removed from the vessel 1 and discarded through line 15. Cooled sterile sauce is added through a transfer line 30 and valve 31 to the cool sterile solids remaining in vessel 1. This vessel is then rotated to effect mixing of the sauce and solids components of the finished product.

EXAMPLE 2

The entrée "Chicken à la king" is prepared by loading the vessel 1 with a mixture composed of 65% chicken meat, 20% mushroom, 6% red peppers, 3% green peppers, 3% onions and 3% peas. A mixture consisting of vegetable oil and flour and chicken stock is added so that it constitutes 15% of the total. Vessel 1 is rotated at 3 r.p.m. and steam is introduced through nozzle 8 to maintain the headspace temperature at 130° C.

After approximately 1 minute and 30 seconds, preheated stock from a previous batch at 130° C. held in vessel 22, is injected into the vessel 1 via pump 23 valve 14 and nozzle 8.

The rotation of vessel 1 is continued and steam is introduced until the $F_o$ reaches the pre-set value. Rotation during the second part of this heating process is intermittent, the vessel turning one complete revolution every 20 seconds and stopping for 40 seconds before recommencing. At the end of the heating process, cold water is circulated in the jacket of vessel 1 and the rotation of the vessel returns to a continuous regime. When the temperature of the solids, condensate and lubricant reach 60° C. the filter head 29 is lowered, the air pressure in the headspace reduced to 12 to 15 psig and the liquors removed, via line 9 valve 21 to vessel 22. Liquor recovered in vessel 22 is available for reheating ready for injection during the next cycle or it may be cooled and stored in a sterile condition. Cooled sterile sauce is added through a transfer line 30 and valve 31 to the cool sterile solids remaining in vessel 1. This vessel is then rotated to effect mixing of the sauce and solids components of the finished product.

Various modifications may be made within the scope of the invention as defined by the appended claims.

We claim:

1. A batch process for the sterilization of particulate solid materials, in which a batch of particulate solid material to be sterilized is introduced with a small amount of lubricant liquid into a rotary vessel shaped so that rotation of the vessel imparts a tumbling action to the solid material; the solid material is heated in the vessel by direct introduction of pressurized steam into the vessel to condense therein while rotating the vessel to subject the material to a tumbling action; additional lubricant liquid is added to the heated solids by injection under pressure into the pressurized vessel at a temperature in excess of the temperature of the solids and above the atmospheric boiling temperature of the lubricant liquid but below the boiling temperature corresponding to the pressure in the vessel; the lubricant liquids and solid material are held at a sterilization temperature while maintaining the tumbling action; and the sterilized solid material is withdrawn from the vessel under aseptic conditions.

2. A process as claimed in claim 1, in which the lubricant liquid is water.

3. A process as claimed in claim 1, in which the lubricant liquid is liquid recovered from a previously processed batch and reheated before injection.

4. A process as claimed in claim 1, in which the lubricant liquid is an oil.

5. A process as claimed in claim 1, in which the lubricant liquid is an emulsion of oil and water.

6. A batch process as claimed in claim 1, in which the solid material is cooled before withdrawal from the vessel.

7. A batch process as claimed in claim 6, in which the cooling takes place under positive pressure.

8. A batch process as claimed in claim 7, in which vapour condensed in the vessel during cooling is replaced by sterile gas fed in through a sterilizing filter.

9. A batch process as claimed in claim 1, in which the vessel is rotated continuously during the heat treatment.

10. A batch process as claimed in claim 1, in which the vessel is intermittently rotated on a periodic basis during the heat treatment.

11. A process as claimed in claim 1, in which the lubricant liquid is injected from a sterile heating circuit and withdrawn from the vessel and returned to the sterile heating circuit.

* * * * *